United States Patent
Araie et al.

(10) Patent No.: US 6,294,544 B1
(45) Date of Patent: Sep. 25, 2001

(54) PERIPHERAL CIRCULATION IMPROVERS FOR OPHTHALMIC TISSUES CONTAINING DIHYDROPYRIDINES

(75) Inventors: Makoto Araie; Ken Tomita, both of Tokyo (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/147,176

(22) PCT Filed: Apr. 21, 1997

(86) PCT No.: PCT/JP97/01367

§ 371 Date: Nov. 13, 1998

§ 102(e) Date: Nov. 13, 1998

(87) PCT Pub. No.: WO97/40834

PCT Pub. Date: Jun. 11, 1997

(30) Foreign Application Priority Data

Apr. 26, 1996 (JP) ........................ 8-108264

(51) Int. Cl.$^7$ .................................. A61K 31/435
(52) U.S. Cl. ........................... 514/277; 514/912
(58) Field of Search ...................... 514/277, 912

(56) References Cited

U.S. PATENT DOCUMENTS 5,431,907 * 7/1995 Abelson et al. ............ 424/78.04

FOREIGN PATENT DOCUMENTS

WO 93/23082    11/1993 (EP).

OTHER PUBLICATIONS

Chemical Abstracts 124: 75952. Stone et al., 1995.*

* cited by examiner

*Primary Examiner*—Zohreh Fay
(74) *Attorney, Agent, or Firm*—Oblon, Spivak, McClelland, Maier & Neustadt, P.C.

(57) ABSTRACT

The present invention provides a peripheral ocular circulation ameliorant which contains dihydropyridines represented by the general formula (I) or their medicinally acceptable salts as active ingredients

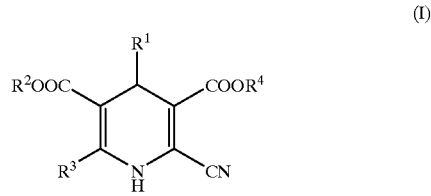

(where $R^1$ is a nitrophenyl group and $R^2$, $R^3$, and $R^4$ are lower alkyl groups), and particularly provides an optic disc blood flow ameliorant, choroidal blood flow ameliorant, retinal blood flow ameliorant, and accordingly, therapeutics for visual field defects associated with normal intraocular pressure glaucoma as well as for optic neuropathy, retinopathy, retinal-degeneration diseases, etc.

8 Claims, 3 Drawing Sheets

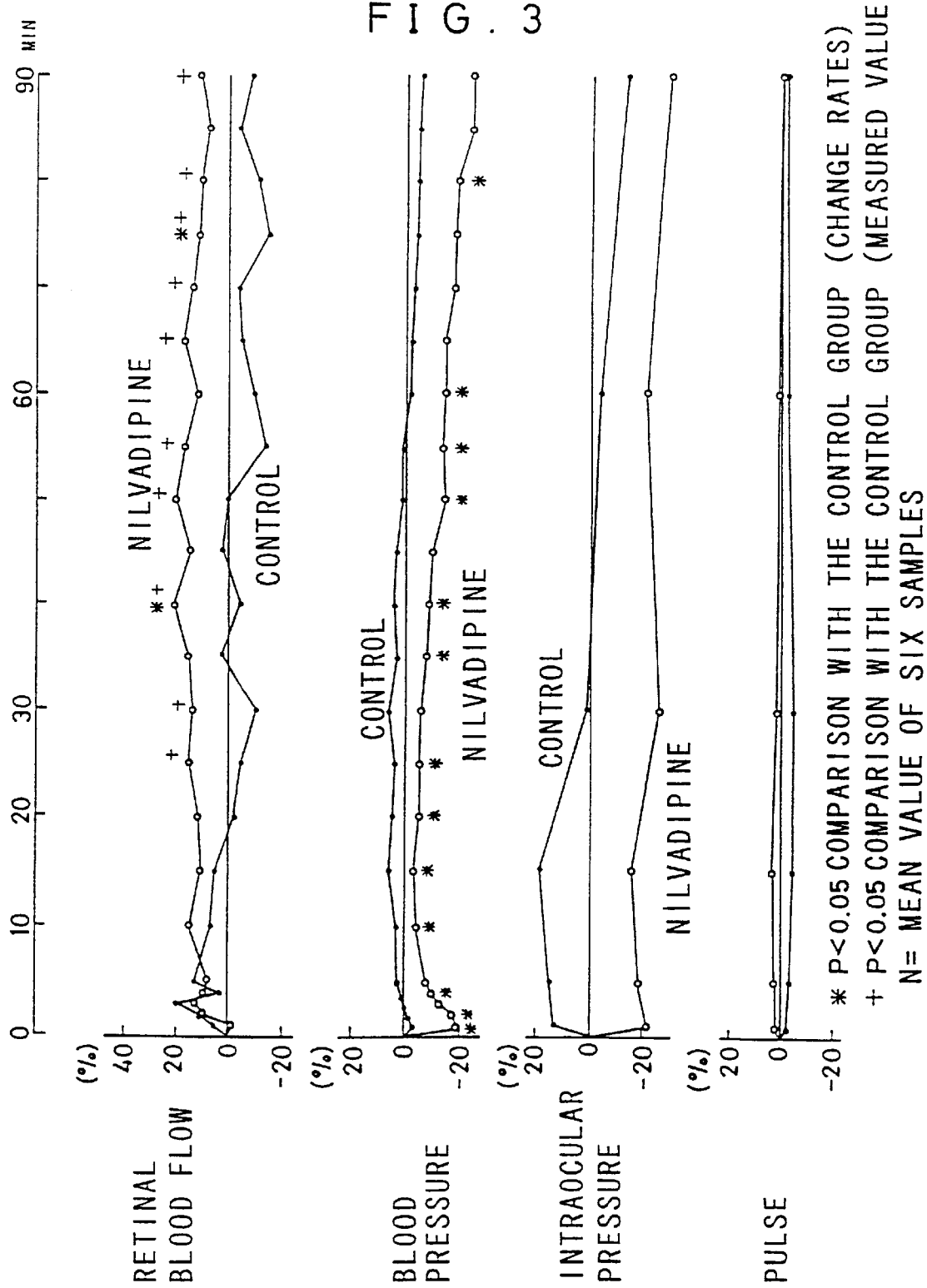

PERIPHERAL CIRCULATION IMPROVERS FOR OPHTHALMIC TISSUES CONTAINING DIHYDROPYRIDINES

FIELD OF THE INVENTION

The present invention relates to a new drug which increases blood flow in the peripheral vessels supplying ocular tissues including the optic disc, choroid, and retina, and thereby shows a therapeutically effective action on visual field defects associated with normal intraocular pressure glaucoma as well as on optic neuropathy, retinopathy, retinal-degeneration diseases, etc.

DESCRIPTION OF THE BACKGROUND

Dihydropyridines are represented by the following general formula (I):

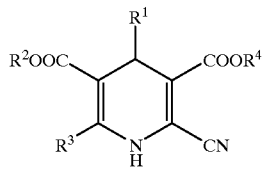

(I)

(where $R^1$ nitrophenyl group and $R^2$, $R^3$, and $R^4$ are all lower alkyl groups). Among these dihydropyridines, the compound with a 3-nitrophenyl group as $R^1$, an isopropyl group as $R^2$, and methyl groups as $R^3$ and $R^4$ is called nilvadipine. It is publicly known as a calcium antagonist, and has had wide clinical usage, for example, as a hypotensive drug. Recently, nicardipine (hydrochloride), another calcium antagonist, has been shown to increase peripheral blood flow in the retina of rabbits. In the case of nilvadipine, however, there had been no information about its effects on the peripheral circulation of the retina or its therapeutic actions on ophthalmic diseases.

SUMMARY OF THE INVENTION

These inventors have studied pharmacological effects of nilvadipine on the peripheral ocular circulation to explore new possible ophthalmologic applications for nilvadipine which is already known as a safe drug with few side effects.

Studies on the pharmacological effects of nilvadipine on the peripheral ocular circulation revealed that it is highly effective in increasing blood flow in the optic disc, choroid, and retina. In particular, the effect on the optic disc in increasing its blood flow is one that has not been seen with nicardipine (hydrochloride). Thus, it became apparent that these pharmacological effects of nilvadipine are expected to exert an excellent therapeutic effect in the clinical treatment of visual field defects associated with normal intraocular pressure glaucoma as well as of optic neuropathy, retinopathy, retinal-degeneration-related diseases, etc.

DETAILED DESCRIPTION OF THE PREFERRED EMBODIMENTS

In a first aspect of the present invention, an optic disc blood flow ameliorant includes dihydropyridines represented by the general formula (I):

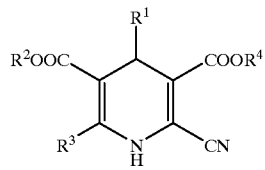

(I)

(where $R^1$ is a nitrophenyl group and $R^2$, $R^3$, and $R^4$ are all lower alkyl groups), especially 6-cyano-5-methoxycarbonyl-2-methyl-4-(3-nitrophenyl)-1,4-dihydropyridine-3-carboxylic acid isopropyl ester (generic name: nilvadipine), or their medicinally acceptable salts, in combination with medicinally acceptable vehicles.

In a second aspect of the present invention, a choroidal blood flow ameliorant includes the above-mentioned dihydropyridines, or their medicinally acceptable salts, in combination with medicinally acceptable vehicles.

In a third aspect of the present invention, a retinal blood flow ameliorant includes the above-mentioned dihydropyridines, or their medicinally acceptable salts, in combination with medicinally acceptable vehicles.

More specifically, this invention, as a drug which includes the above-mentioned dihydropyridines including nilvadipine, or their medicinally acceptable salts, in combination with medicinally acceptable vehicles, is intended to provide a therapeutic agent for clinical treatment of visual field defects associated with normal intraocular pressure glaucoma as well as of optic neuropathy, retinopathy, retinal-degeneration-related diseases, etc.

BRIEF DESCRIPTION OF THE DRAWINGS

FIG. 3 graphically shows the effect of nilvadipine administration on the peripheral blood flow velocity in the retina.

THE BEST MODE FOR CARRYING OUT THE INVENTION

Figure 1:
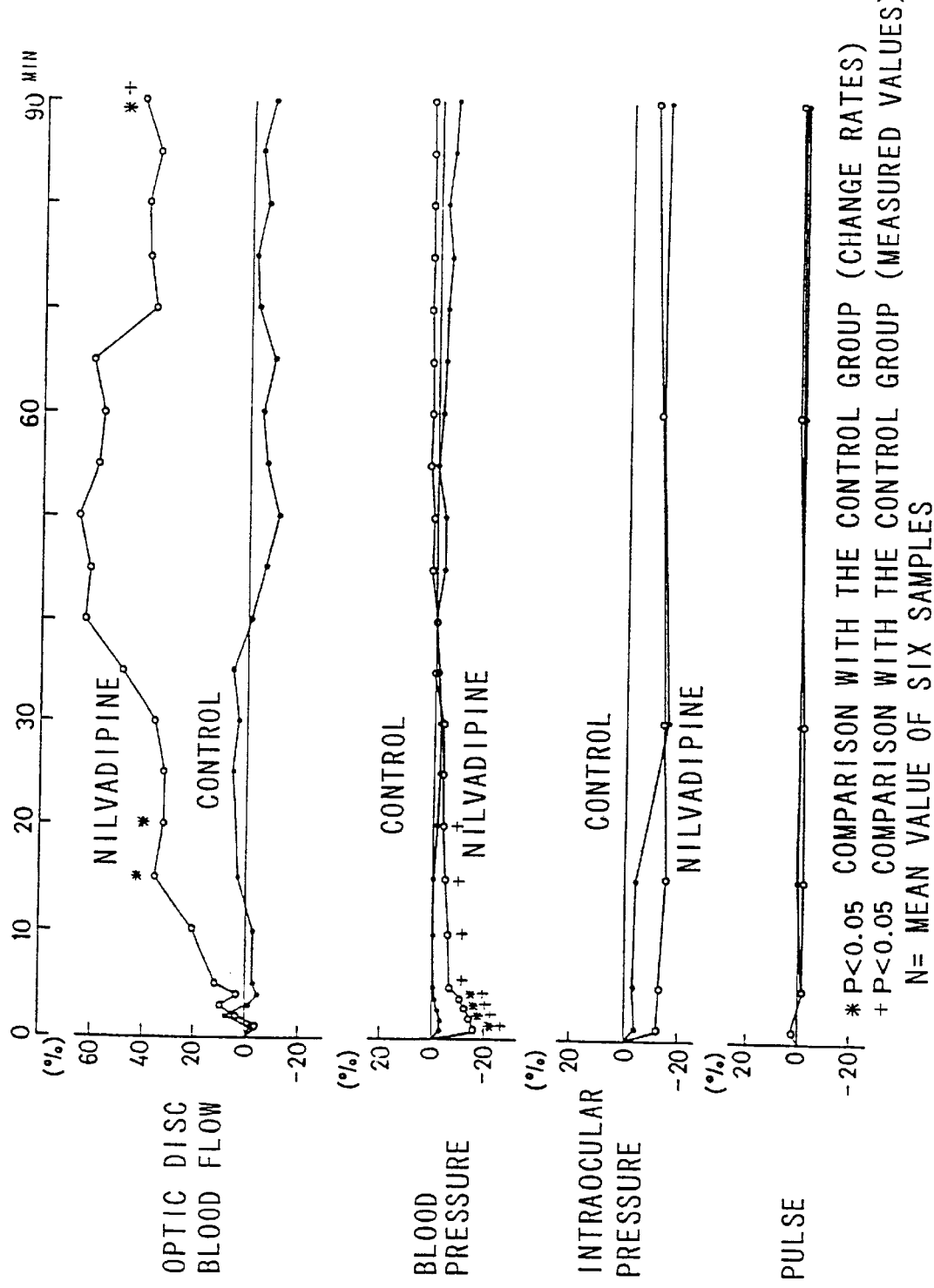
FIG. 1 graphically shows the effect of nilvadipine administration on the peripheral blood flow velocity in the optic disc.

Further details of the invention will be described below.

The term "optic disc blood flow ameliorant, etc." as used herein will be used to represent in general the above-mentioned optic disc blood flow ameliorant, choroidal blood flow ameliorant, retinal blood flow ameliorant, and therapeutic agents for visual defects associated with normal intraocular pressure glaucoma as well as for optic neuropathy, retinopathy, retinal degeneration diseases, etc.

The above-mentioned optic neuropathy includes ischemic optic neuropathy such as arteriosclerotic obstruction of the central retinal vein or central retinal artery and stenosis of the retinal arterioles associated with renal retinopathy, toxemic retinopathy of pregnancy, etc. The above-mentioned retinopathy includes diabetic retinopathy.

In the structure of the dihydropyridines used for the invention and represented by the general formula (I),

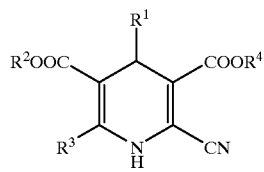

(I)

2-nitrophenyl, 3-nitrophenyl, or 4-nitrophenyl may function as the nitrophenyl group represented by $R^1$. Methyl, ethyl, propyl, isopropyl, butyl, t-butyl, pentyl, and/or hexyl may functions as the lower alkyl groups represented by $R^2$, $R^3$, and $R^4$.

The preferred medicinally acceptable salts of the dihydropyridines (I) include the following commonly used non-toxic salts: organic acid adducts such as acetates, trifluoroacetates, maleates, tartrates, methansulfonates, benzenesulfonates, formates, toluenesulfonates, etc.; inorganic acid adducts such as hydrochlorides, hydrobromates, hydroiodates, sulfates, nitrate, phosphates, etc.; and salts with acidic amino acids such as aspartates, glutamates, etc.

The "optic disc blood flow ameliorant, etc." of the present invention will be formulated into solid, semi-solid, or liquid forms for oral or parenteral use by adding dihydropyridines (I), typically nilvadipine, or their medicinally acceptable salts as active ingredients to medicinally acceptable inorganic or organic vehicles.

Thus, the drugs of the present invention can be provided as formulations either for oral use or for parenteral use, so that the best formulation can be chosen according to the route of administration or subjects to be treated. Tablets, pills, powders, granules, soft and hard capsules, pellets, sublingual tablets, troches, and various solutions, etc. are examples of formulations for oral use. Formulations suitable for parenteral use include injections, drip infusions, transfusions, suspensions, oils, emulsions, and suppositories, etc. Formulations suitable for topical use include eye ointments, eye drops, and sprays, etc.

The active compounds of the present invention can be formulated through the conventional methods of formulation by appropriately using surfactants, fillers, colors, flavors, preservatives, stabilizers, buffer agents, suspending agents, tonicity agents, and other commonly used vehicles of which common use is medicinally acceptable. It is also possible to formulate the active compounds into recently developed various drug delivery systems which have been abbreviated to DDSs.

The dose of the above-mentioned dihydropyridines (I), typically nilvadipine, should appropriately be determined according to the type of formulation, method of administration, age and weight of the patient, severity of symptoms, etc. Usually, the oral administration dose may be about 0.1 to 100 mg per day, preferably 1 to 16 mg per day. An effective single dose may be chosen from the range between about 0.001 and 1 mg per kg body weight, preferably between 0.01 and 0.16 mg per kg body weight.

In the following, the usefulness of nilvadipine for the "optic disc blood flow ameliorant, etc." will be described.

The usefulness of nilvadipine was investigated as outlined below. There were no drug safety problems.

[A] Studies in Rabbits

1. Methods: The velocity of peripheral blood flow in the optic disc, choroid, and retina of anesthetized normal rabbits was measured by the laser speckle method. (6 rabbits per group)

2. Administration: A single intravenous injection of nilvadipine at 3.2 µg/kg was administered.

Figure 2:
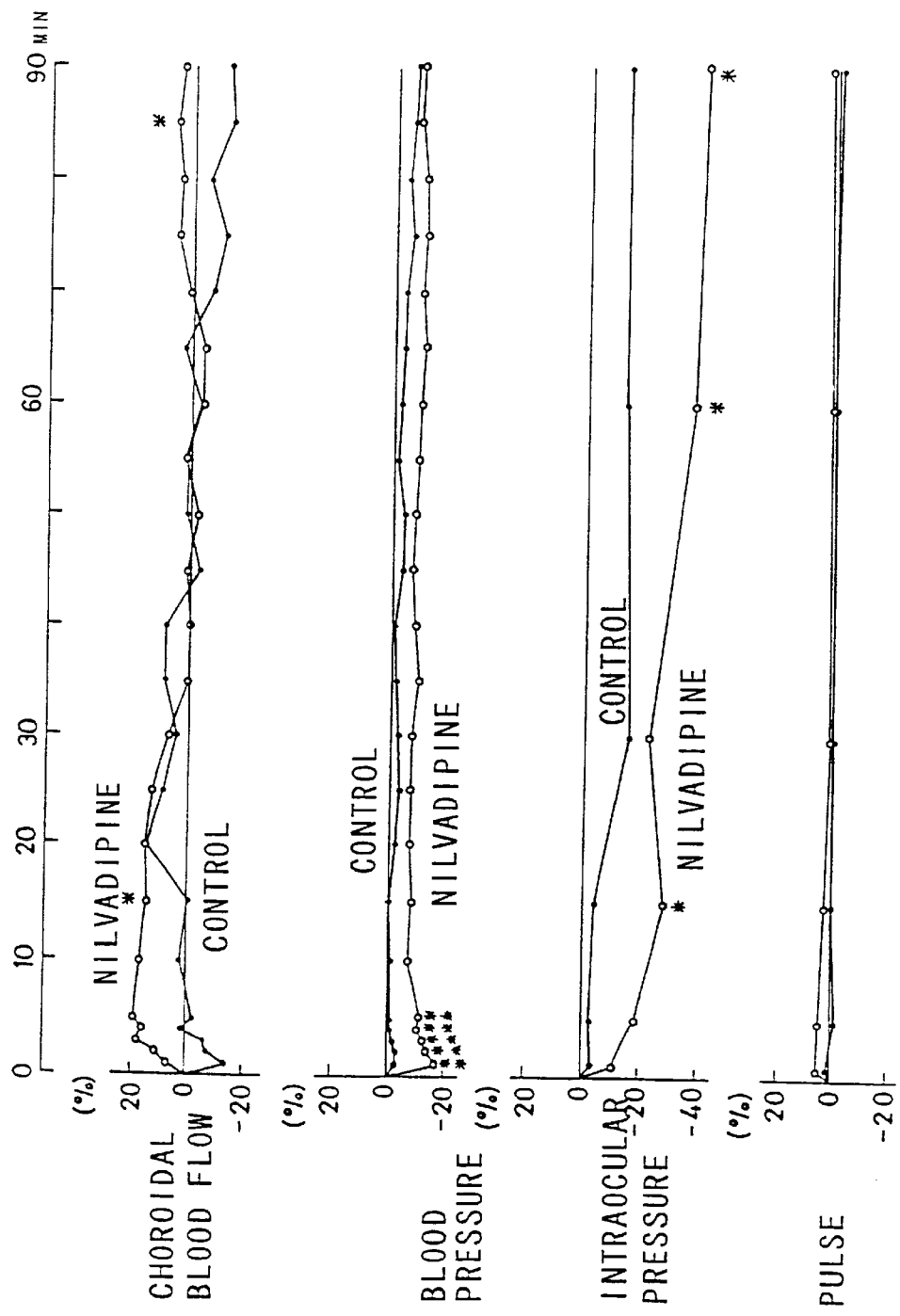
FIG. 2 graphically shows the effect of nilvadipine administration on the peripheral blood flow velocity in the choroid.

3. Results: Nilvadipine increased peripheral blood flow in the optic disc, choroid, and retina. The increase was especially marked in the optic disc, and it reached the maximum of 43% (statistically significant enhancement). However, increase was insignificant in some cases, and there was more than 60% increase at some occasions (see FIGS. 1 to 3). This blood flow increase in the optic disc was a strong action, particular to nilvadipine and not characteristic of other calcium antagonists.

[B] Studies in Humans

1. Methods: In 2 women in their fifties, the velocity of peripheral blood flow in the optic disc and retina was measured by the laser speckle method.

2. Administration: Two mg (b.i.d.) of nilvadipine was orally administered for about 4 weeks.

3. Results: Two weeks after the start of nilvadipine administration, the velocity of peripheral blood flow in the optic disc and choroid increased by about 20% in both women (see Tables 1 and 2). Blood pressure showed a tendency to decrease slightly, but remained within the normal range for both subjects.

TABLE 1

M

| item | | before administration | 2 weeks after | 6 weeks after | 9 weeks after |
|---|---|---|---|---|---|
| optic | right | 16.1 | 20.1(+25%) | 18.2(+13%) | 18.2(+13%) |
| disc | left | 24.4 | 28.5(+17%) | 22.5(−8%) | 18.8(−23%) |
| Retia | right | 17,6 | 20.8(+18%) | 20.4(+16%) | 25.8(+47%) |
| | left | 19.2 | 21.0(+9%) | 20.0(+4%) | 25.1(+31%) |
| blood pressure | | 156/91 | 141/83 | 129/82 | 135/83 |
| pulse | | 96 | 94 | 91 | 91 |

TABLE 2

T

| item | | Before Administration | 2 weeks after | 4 weeks after |
|---|---|---|---|---|
| optic | right | 17.4 | 18.0(+3%) | 16.5(−5%) |
| disc | left | 19.1 | 20.5(+7%) | 22.5(+18%) |
| retia | right | 26.0 | 28.9(+11%) | 30.3(+17%) |
| | left | 23.1 | 28.2(+22%) | 28.5(+23%) |
| blood pressure | | 129/80 | 128/73 | 113/66 |
| pulse | | 78 | 93 | 81 |

Some examples of the drugs of the present invention will be described below.

EXAMPLE 1

| Nilvadipine | 100 g |
|---|---|
| Hydroxypropyl methylcellulose | 500 g |

Nilvadipine was dissolved in absolute ethanol (5 liters). To the resultant solution, hydroxypropyl methylcellulose was added to prepare a suspension. The organic solvent was removed under reduced pressure, and a composition of dispersed solid matter was reduced pressure, and a composition of dispersed solid matter was obtained.

EXAMPLE 2

| Nilvadipine | 100 g |
|---|---|
| Hydroxypropyl methylcellulose | 500 g |
| Sucrose | 9.4 kg |

To the suspension containing nilvadipine and hydroxypropyl methylcellulose in absolute ethanol (5 liters), sucrose was added, and the mixture was stirred. The organic solvent was removed under reduced pressure, and a composition of dispersed solid matter was obtained. This composition was prepared into fine subtilaes through the conventional process.

EXAMPLE 3

| Niivadipine | 100 g |
|---|---|
| Hydroxypropyl methylceilulose | 500 g |
| Lactose | 6.87 kg |
| Lower substituted hydroxypropyl methyl cellulose | 1.5 kg |
| Magnesium stearate | 30 g |

To the suspension containing nilvadipine and hydroxypropyl methylcellulose in absolute ethanol (5 liters), lactose and lower substituted hydroxypropyl cellulose were added, and the mixture was stirred. The organic solvent was removed under reduced pressure, and a composition of dispersed solid matter was obtained. This composition was prepared into granules through the conventional process, and then further prepared into tablets through the conventional process. The resultant tablets contain 2 mg of nilvadipine per tablet.

EXAMPLE 4

The tablets obtained in Example 3 were film-coated with a layer consisting of hydroxypropyl methylcellulose (5.1 mg), titanium dioxide (1.6 mg), polyethylene glycol 6000 (0.8 mg), talc (0.4 mg), and yellow iron oxide (0.1 mg) through the conventional process. The resultant film-coated tablets contain 2 mg of nilvadipine per tablet.

INDUSTRIAL APPLICABILITY

As mentioned above, these invented drugs containing dihydropyridines (I), typically nilvadipine, increase blood flow in the peripheral vessels supplying the optic disc, choroid, retina, etc. and thereby show a therapeutically effective action on visual field defects associated with normal intraocular pressure glaucoma as well as on optic neuropathy, retinopathy, retinal-degeneration diseases, etc. They are exceptional in the aspect of safety as well. Therefore, they are suitable for improving peripheral ocular circulation, especially in the treatment of visual field defects associated with normal intraocular pressure glaucoma as well as for optic neuropathy, retinopathy, retinal-degeneration diseases, etc.

What is claimed is:

1. A method of increasing bloodflow in peripheral vessels supplying ocular tissues, comprising administering an effective amount of nilvadipine, or a pharmaceutically salt thereof, to a mammal in need thereof.

2. The method of claim 1, wherein said mammal is a human.

3. The method of claim 1, wherein said effective amount is about 0.001 to 1 mg per kg of body weight.

4. The method of claim 3, wherein said effective amount of about 0.01 to 0.16 mg per kg of body weight.

5. A method of ameliorating peripheral ocular circulation, which comprises administering an effective amount of nilvadipine, or a pharmaceutically acceptable salt thereof, to a mammal in need thereof.

6. The method of claim 5, wherein said mammal is human.

7. The method of claim 6, wherein said effective amount is about 0.001 to 1 mg per kg of body weight.

8. The method of claim 7, wherein said effective amount is about 0.01 to 0.16 mg per kg of body weight.

* * * * *